United States Patent [19]

Fischer et al.

[11] Patent Number: 4,740,613

[45] Date of Patent: Apr. 26, 1988

[54] PREPARATION OF 4-PENTENOATES

[75] Inventors: Rolf Fischer, Heidelberg; Uwe Vagi, Speyer, both of Fed. Rep. of Germany

[73] Assignee: BASF Aktiengesellschaft, Ludwigshafen, Fed. Rep. of Germany

[21] Appl. No.: 24,676

[22] Filed: Mar. 11, 1987

[51] Int. Cl.[4] .................. C07C 67/27; C07C 64/53
[52] U.S. Cl. ........................... 560/205; 560/217
[58] Field of Search ........................ 560/205, 217

[56] References Cited

U.S. PATENT DOCUMENTS

| | | | |
|---|---|---|---|
| 3,182,077 | 5/1965 | Dever et al. | 560/205 |
| 3,966,798 | 6/1976 | Intille | 560/205 |
| 4,529,815 | 7/1985 | Schneider | 560/208 |
| 4,561,942 | 12/1985 | Schneider et al. | 560/205 |

FOREIGN PATENT DOCUMENTS

| | | | |
|---|---|---|---|
| EP41343 | 12/1981 | European Pat. Off. | 560/205 |
| EP40958 | 12/1981 | European Pat. Off. | 560/205 |
| 3521381 | 12/1986 | Fed. Rep. of Germany | 560/205 |
| 2027714 | 2/1977 | Japan | 560/205 |

OTHER PUBLICATIONS

Chemical Abstracts, vol. 82, No. 1, 19, May 12, 1975.

Primary Examiner—Paul J. Killos
Attorney, Agent, or Firm—Keil & Weinkauf

[57] ABSTRACT

4-Pentenoates of the formula

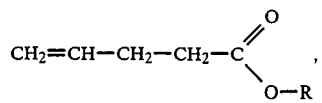

where R is alkyl of from 1 to 6 carbon atoms, are prepared by a process in which 5-methylbutyrolactone of the formula

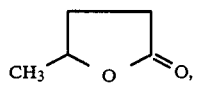

is reacted with an alcohol of the formula

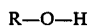

III, where R has the above meaning, at from 150° to 400° C. in the presence of an acidic catalyst.

6 Claims, No Drawings

PREPARATION OF 4-PENTENOATES

The present invention relates to a process for the preparation of 4-pentenoates by reacting 5-methylbutyrolactone with an alcohol in the presence of an acidic catalyst at from 150° to 400° C.

It has been disclosed that 3-pentenoates can be isomerized to 4-pentenoates at from 100° to 150° C. in the presence of acidic ion exchangers or acidic zeolites which contain noble metals of group eight of the periodic table, such as palladium, rhodium or ruthenium (Germain Laid-Open Application DOS No. 3,317,163). Thus, isomer mixtures which, in addition to unconverted methyl 3-pentenoate and small amounts of 2-pentenoates, contain 8% by weight of the desired methyl 4-pentenoate are obtained starting from, for example, methyl 3-pentenoate (70% trans, 30% cis). The 4-pentenoate can be isolated from such isomer mixtures by azeotropic distillation with water (German Laid-Open Application DOS No. 3,412,295). The disadvantage of this procedure is that the 4-pentenoate content of the isomer mixtures cannot be increased substantially above 8% by weight. Consequently, isolation of the 4-pentenoate and recycling of the 2- and 3-pentenoates entail considerable expense in terms of distillation.

It is an object of the present invention to provide a process in which higher 4-pentenoate contents are achieved in the mixture of isomeric pentenoates.

We have found that this object is achieved by a process for the preparation of 4-pentenoates of the formula

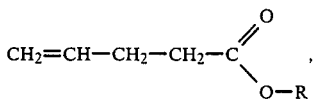   I where R is alkyl of 1 to 6 carbon atoms, wherein 5-methylbutyrolactone of the formula

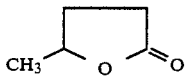   II is reacted with an alcohol of the formula

R—OH   III, where R has the above meaning, at from 150° to 400° C. in the presence of an acidic catalyst.

The formation of pentenoates, in particular 4-pentenoates, in the reaction of 5-methylbutyrolactone with an alcohol in the presence of an acidic catalyst is surprising and has not been described to date. Thus, in an attempt to cleave butyrolactone under the conditions according to the invention to give methyl 3-butenoate, only small amounts of the desired ester were obtained (see Comparative Example 1).

It was also not forseeable that, in the cleavage of 5-methylbutyrolactone with an alcohols in the presence of an acidic catalyst, up to 38% (based on the sum of all pentenoates) of the 4-pentenoate and only about 10% (based on 4-pentenoate) of the 2-cis-pentenoate would be formed in addition to cis- and trans-3-pentenoates.

It is also noteworthy that lactone cleavage to give alkenecarboxylates takes place preferentially to ether formation from the participating alcohols, which is likewise acid-catalyzed.

For the preparation of methyl 4-pentenoate, the reaction according to the invention can be represented by the following equation:

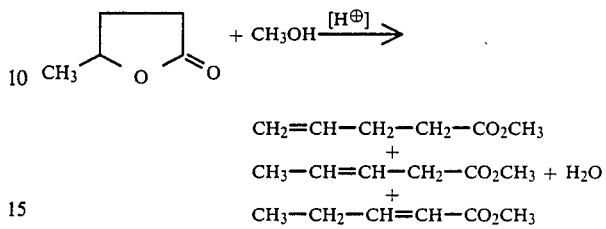

$$CH_2=CH-CH_2-CH_2-CO_2CH_3$$
$$+$$
$$CH_3-CH=CH-CH_2-CO_2CH_3 + H_2O$$
$$+$$
$$CH_3-CH_2-CH=CH-CO_2CH_3$$

In addition to methyl 4-pentenoate, methyl 3- and 2-pentenoates are formed and, with the exception of methyl 2-cis-pentenoate, can be separated from methyl 4-pentenoate by distillation.

Examples of suitable alcohols of the formula III are methanol, ethanol, n-propanol, isopropanol, tert-butanol, n-butanol, isobutanol, sec-butanol, n-pentanol and n-hexanol, methanol, ethanol and propanols being particularly useful.

The molar ratio of 5-methylbutyrolactone II to the alcohol III is advantageously from 1:0.5 to 1:10, in particular from 1:1 to 1:5.

The reaction is carried out at from 150° to 400° C., preferably from 200° to 400° C., in particular from 250° to 350° C., advantageously under from 1 to 100, in particular from 1 to 10, bar.

Examples of suitable acidic catalysts are acidic oxides of elements of main groups III and IV and subgroups IV and VI of the periodic table, as well as protic and Lewis acids.

The reaction can be carried out batchwise or continuously as a fixed bed reaction using fixed bed catalysts, for example by the liquid phase or trickle-bed procedure in the liquid phase or gas phase, for example by the fluidized bed method, or using a fixed bed catalyst suspended in the liquid phase.

Examples of suitable acidic catalysts are heterogeneous catalysts, eg. silica in the form of silica gel, kieselguhr or quartz, as well as titanium dioxide, zirconium dioxide, phosphorus pentoxide, vanadium pentoxide, boron trioxide, alumina, chromium oxides, molybdenum oxides, tungsten oxides, and mixtures of these. Zeolites, in particular A, X and Y zeolites or pentasil zeolites in the acidic form, are also suitable.

If 5-methylbutyrolactone is reacted over a fixed bed catalyst in the gas phase, a space velocity of from 0.1 to 10, in particular from 0.1 to 5, g of 5-methylbutyrolactone per g of catalyst per hour is advantageously used.

It is also possible, in the liquid phase, to use an acidic catalyst dissolved to form a homogeneous solution.

For example, mineral acids such as sulfuric acid, phosphoric acid, hydrochloric acid, nitric acid or hydrobromic acid and sulfonic acids such as benzenesulfonic acid or p-toluenesulfonic acid are suitable. The molar ratio of 5-methylbutyrolactone to mineral acid is, for example, from 1:0.001 to 1:1, in particular from 1:0.01 to 1:0.1.

The reaction of 5-methylbutyrolactone II with the alcohol in the liquid phase is preferably carried out, for example, by heating a mixture of II and the particular alcohol III to the desired reaction temperature in the presence of a suspended fixed bed catalyst or of a catalyst dissolved to form a homogeneous solution. When the necessary reaction time has elapsed, the reaction mixture is cooled and the acidic catalyst is removed, for example by filtration or neutralization. The reaction mixture is then subjected to fractional distillation to obtain the desired 4-pentenoate.

In a preferred embodiment of the novel process in the gas phase, for example, a mixture of 5-methylbutyrolactone and the particular alcohol is first vaporized and then passed, with or without an inert gas, such as nitrogen, carbon dioxide or argon, at the desired reaction temperature, in the form of a gas, over a fixed bed catalyst or in particular a catalyst fluidized in an upward and downward direction. The reacted mixture is condensed by means of a suitable cooling apparatus and then worked up by fractional distillation. Here, it is advisable initially to distill off the mixture of pentenoates (boiling point of the methyl ester, for example, 129°–143° C./1013 mbar) from any unconverted 5-methylbutyrolactone (boiling point 207°–208° C./1013 mbar) and then to isolate the 4-pentenoate from the 2- and 3-pentenoates. Any 5-methylbutyrolactone recovered is advantageously recycled to the lactone cleavage.

2- and 3-pentenoates can be converted back to 5-methylbutyrolactone by hydrolysis to the corresponding pentenoic acids in the presence of sulfuric acid as a catalyst (R. P. Linstead, J. Chem. Soc. 1932, pages 115–129).

Compared with the isomerization of 3-pentenoates to 4-pentenoates, the novel process for the preparation of 4-pentenoates has the advantage that higher 4-pentenoate contents are achieved in the mixture of isomeric pentenoates. This results in a more advantageous procedure for isolation of the 4-pentenoates. Another advantage is that, instead of noble metal catalysts which contain palladium, ruthenium or rhodium, oxides of non-noble metals can be used as catalysts.

The 4-pentenoates obtainable by the novel process are useful intermediates which can be converted to 5-formylvalerates by low pressure hydroformylation in the presence of Rh compounds as catalysts (German Laid-Open Application DOS No. 3,317,164). 5-Formylvalerates can be converted to caprolactam, without producing ammonium sulfate, by hydrogenation under aminating conditions and cyclization of the resulting aminocaproates.

The Examples which follow illustrate the process according to the invention.

EXAMPLE 1

A mixture of 8.3 g/hour of 5-methylbutyrolactone and 2.7 g/hour of methanol (molar ratio 1:1) was pumped into an evaporator and passed from there, in the form of a gas and together with 3 liters of nitrogen, over 5 g of an $Al_2O_3$ catalyst at 300° C. The gaseous reacted mixtures were condensed, weighed and analyzed by gas chromatography. Table 1 shows the composition of the reacted mixtures after various reaction times. The lactone conversion was about 25%, and the ratio of methyl 4-pentenoate to the sum of all pentenoates formed was from 33 to 36%.

In reaction times from 916 to 1008 hours, 970 g of a lactone/methanol mixture (732 g (7.31 moles) of lactone) were passed over the catalyst and 906 g of reacted mixture were condensed. 583 g (5.82 moles) of unconverted 5-methylbutyrolactone and a mixture of 57 g (0.5 mole) of methyl 4-pentenoate, 63 g (0.555 mole) of methyl cis- + trans-3-pentenoate, 6 g (0.05 mole) of methyl 2-cispentenoate and 39 g (0.34 mole) of methyl 2-transpentenoate were obtained from this reacted mixture by fractional distillation over a spinning band column. The conversion was 20%, the selectivity with respect to methyl 4-pentenoate was 90% (2-cis-pentenoate was considered as the loss), and the ratio of methyl 4-pentenoate to the sum of all pentenoates formed was 34.5%. The non-distillable residue from 906 g of reacted mixture was only 3 g.

COMPARATIVE EXAMPLE 1

When Example 1 was repeated using butyrolactone instead of 5-methylbutyrolactone at 300° C. and a molar ratio of lactone to methanol of 1:3, the reacted mixture obtained after a reaction time of 3 hours consisted of 94% of unconverted butyrolactone, 3.8% of methyl cis- and trans-2-butenoate and only 0.6% of the desired methyl 3-butenoate.

EXAMPLES 2 TO 6

Under the same conditions as in Example 1, 10 g of a 5-methylbutyrolactone/methanol mixture having the molar ratio stated in Table 2 was passed in the form of a gas over 5 g of the particular catalyst. The composition of the reacted mixtures is shown in the table.

TABLE 1

Methyl 4-pentenoate (4-PAE) by cleavage of 5-methylbutyrolactone with methanol
% by area (without $CH_3OH$)[1]

| Reaction time [h] | 4-PAE | Σ 3-PAE | 2-cis-PAE | 2-tr.-PAE | 5-methyl-butyro-lactone | Other products | $\frac{\text{4-PAE}}{\Sigma \text{ PAE}} \times 100$ |
|---|---|---|---|---|---|---|---|
| 25 | 10.7 | 12.3 | 1.2 | 7.1 | 65.0 | 3.7 | 34.2 |
| 118 | 8.5 | 9.0 | 0.8 | 5.1 | 74.7 | 1.9 | 36.3 |
| 212 | 8.4 | 9.0 | 0.8 | 5.1 | 75.6 | 1.1 | 36.1 |
| 332 | 9.0 | 9.5 | 0.9 | 5.4 | 73.9 | 1.3 | 36.3 |
| 550 | 8.4 | 10.0 | 0.9 | 5.9 | 72.9 | 1.9 | 33.3 |
| 646 | 8.6 | 9.5 | 0.8 | 5.5 | 73.3 | 2.3 | 35.2 |
| 742 | 8.2 | 9.3 | 0.8 | 5.4 | 74.7 | 1.6 | 34.6 |
| 838 | 9.0 | 10.6 | 0.9 | 6.1 | 70.5 | 2.9 | 33.8 |
| 934 | 9.5 | 10.0 | 0.8 | 5.8 | 73.0 | 1.9 | 33.9 |
| 1006 | 8.0 | 9.9 | 0.8 | 5.6 | 73.7 | 2.0 | 32.9 |

[1]GC capillary column Silar 5 CP, 25 m
PAE = methyl pentenoate

TABLE 2

| | | | | Methyl 4-pentenoate (4-PAE) by cleavage of 5-methylbutyrolactone with methanol in the presence of different catalysts | | | | | | |
|---|---|---|---|---|---|---|---|---|---|---|
| Example | Catalyst | Reaction temperature [°C.] | Molar ratio lactone: CH$_3$OH | Reaction time [h] | 4-PAE | Σ 3-PAE | 2-cis-PAE | 2-tr.-PAE | 5-Methyl-butyro-lactone | Other pro-ducts | $\frac{4\text{-PAE}}{\Sigma\,\text{PAE}} \times 100$ |
| 2 | Al$_2$O$_3$/SiO$_2$* | 300 | 1:1 | 2 | 8.0 | 30.9 | 2.9 | 14.4 | 35.5 | 8.3 | 14 |
| 3 | TiO$_2$ | 400 | 1:1 | 2 | 17.0 | 16.7 | 1.7 | 9.2 | 51.5 | 3.9 | 38 |
| 4 | B$_2$O$_3$/Al$_2$O$_3$** | 300 | 1:1 | 6 | 4.4 | 8.8 | 0.6 | 4.1 | 79.9 | 2.2 | 25 |
| 5 | SiO$_2$ | 300 | 1:1 | 6 | 9.1 | 14.0 | 0.7 | 3.8 | 71.0 | 1.4 | 33 |
| 6 | Al$_2$O$_3$ (D 10-10) | 300 | 1:4 | 7 | 14.9 | 15.4 | 1.8 | 10.3 | 53.2 | 4.4 | 35 |

*25% of Al$_2$O$_3$, 75% of SiO$_2$
**45% of B$_2$O$_3$, 55% of γ-Al$_2$O$_3$

We claim:

1. A process for the preparation of a 4-pentenoate of the formula

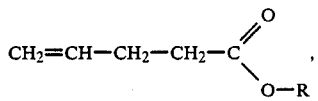   I where R is alkyl of 1 to 6 carbon atoms, wherein 5-methylbutyrolactone of the formula

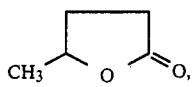   II is reacted with an alcohol of the formula

R—O—H   III, where R has the above meaning, at from 150° to 400° C. in the presence of an acidic catalyst.

2. A process as claimed in claim 1, wherein silica, alumina, titanium dioxide, boron trioxide or a mixture of these is used as the acidic catalyst.

3. A process as claimed in claim 1, wherein 5-methylbutyrolactone and an alcohol of the formula III are used in a molar ratio of from 1:0.5 to 1:10.

4. A process as claimed in claim 1, wherein a temperature of from 200° to 400° C. is maintained.

5. A process as claimed in claim 1, wherein the reaction is carried out in the gas phase.

6. A process as claimed in claim 5, wherein a space velocity of from 0.1 to 10 g of 5-methylbutyrolactone per g of catalyst per hour is maintained.

* * * * *

UNITED STATES PATENT AND TRADEMARK OFFICE
CERTIFICATE OF CORRECTION

PATENT NO. : 4,740,613
DATED : April 26, 1988
INVENTOR(S) : Rolf FISCHER et al.

It is certified that error appears in the above-identified patent and that said Letters Patent is hereby corrected as shown below:

ON THE TITLE PAGE:

Please Add:

-- [30]　Foreign Application Priority Data

March 19, 1986　[DE] Federal Republic of Germany..... 3609139 --

Signed and Sealed this

Thirtieth Day of August, 1988

Attest:

DONALD J. QUIGG

Attesting Officer

Commissioner of Patents and Trademarks